(12) United States Patent
Greenberg et al.

(10) Patent No.: US 7,483,750 B2
(45) Date of Patent: Jan. 27, 2009

(54) TRANSRETINAL IMPLANT AND METHOD OF IMPLANTATION

(75) Inventors: Robert Greenberg, Los Angeles, CA (US); Mark Humayan, La Canada, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 401 days.

(21) Appl. No.: 10/393,887

(22) Filed: Mar. 21, 2003

(65) Prior Publication Data

US 2004/0186533 A1    Sep. 23, 2004

(51) Int. Cl.
*A61N 1/36*    (2006.01)
(52) U.S. Cl. ....................................... 607/54
(58) Field of Classification Search ............. 607/53–54; 623/6.63
See application file for complete search history.

(56) References Cited

U.S. PATENT DOCUMENTS

| | | | |
|---|---|---|---|
| 5,024,223 A | 6/1991 | Chow et al. | |
| 5,109,844 A | 5/1992 | De Juan, Jr. et al. | |
| 5,397,350 A | 3/1995 | Chow et al. | |
| 5,935,155 A | 8/1999 | Humayan et al. | |
| 6,400,989 B1 | 6/2002 | Eckmiller | |
| 6,427,087 B1 | 7/2002 | Chow et al. | |
| 6,458,157 B1 | 10/2002 | Suaning | |
| 2002/0198573 A1 | 12/2002 | Nisch et al. | |
| 2003/0014089 A1* | 1/2003 | Chow et al. | 607/54 |

* cited by examiner

*Primary Examiner*—Kennedy J Schaetzle
(74) *Attorney, Agent, or Firm*—Scott B. Dunbar; Gary D. Schnittgrund; Alessandro Steinfl

(57) ABSTRACT

A retinal implant device to stimulate a retina of an eye thereby producing a specific effect in an eye, such as vision or drug treatment of a chronic condition is described. The retinal device is made of a retinal implant that is positioned subretinally and that contains a multitude of stimulation sites that are in contact with the retina. A connection carries the stimulating electrical signal or drug. The connection passes transretinally through the retina and into the vitreous cavity of the eye, thereby minimizing damage to the nutrient-rich choroid. The lead is attached to a source of drugs or electrical energy, which is located outside the eye. The lead passes through the sclera at a point near the front of the eye to avoid damage to the retina.

28 Claims, 3 Drawing Sheets

TRANSRETINAL IMPLANT AND METHOD OF IMPLANTATION

FEDERALLY SPONSORED RESEARCH

This invention was made with government support under grant No. R24EY12893-01, awarded by the National Institutes of Health. The government has certain rights in the invention.

FIELD OF THE INVENTION

This invention relates to an implantable retinal medical device for subretinal placement and to a method of manufacture of the medical device.

BACKGROUND OF THE INVENTION

Retinal Stimulation

In 1755 LeRoy passed the discharge of a Leyden jar through the orbit of a man who was blind from cataract and the patient saw "flames passing rapidly downwards." Ever since, there has been a fascination with electrically elicited visual perception. The general concepts of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with limited success, early prosthesis devices were large, bulky and could not produce adequate simulated vision to truly aid the visually impaired.

In the early 1930's, Foerster investigated the effect of electrically stimulating the exposed occipital pole of one cerebral hemisphere. He found that when a point at the extreme occipital pole was stimulated, the patient perceived a small spot of light directly in front and motionless (a phosphene). Subsequently, Brindley and Lewin (circa 1968) studied electrical stimulation of the human occipital cortex. By varying the stimulation parameters, these investigators described the location of the phosphenes produced relative to the specific region of the occipital cortex stimulated.

As intraocular surgical techniques advanced, it became possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in efforts to restore vision where blindness is caused by photoreceptor degenerative retinal diseases, such as retinitis pigmentosa or to macular degeneration.

A variety of retinal diseases cause vision loss or blindness by destruction of the choroid, choriocapillaris, and the outer retinal layers. The outer layers include Bruch's membrane and retinal pigment epithelium, the loss of which results in degeneration of the inner retinal photoreceptor layer. These diseases, however, often spare much of the remaining inner retinal layers of the outer nuclear, outer plexiform, inner nuclear, inner plexiform, ganglion cell, and nerve fiber layers.

Efforts to produce vision by retinal electrical stimulation with arrays of stimulating electrodes are primarily placement on the epiretinal or on the subretinal side of the neuroretina.

Attempts have been made to produce vision by stimulating various portions of the retina. One attempt involved an externally powered but internally located photosensitive array device with its photoactive surface and electrode surface on opposite sides. The device was to stimulate the nerve fiber layer via direct placement on this layer from the vitreous body side. The device may need to duplicate the neural signals of the nerve fiber layer. The nerve fiber layer generally runs radially with many layers of overlapping fibers from different portions of the retina making selection of the appropriate nerve fiber to stimulate difficult.

Another device involved a supporting base with a photosensitive material, such as a selenium coating. This device was inserted through an external scleral incision made at the posterior pole such that the device rested between the sclera and choroid or between the choroid and retina. Light stimulation caused ions to be produced that would then theoretically migrate into the retina causing stimulation. No discrete surface structure restricted the directional flow of charges, thereby preventing any resolution capability. Placement of this device between the sclera and choroid would also block the discrete migration of ions to the photoreceptor and inner retinal layers due to the presence of the choroid, choriocapillaris, Bruch's membrane, and the retinal pigment epithelial layer. Placement of the device between the choroid and the retina interposed Bruch's membrane and the retinal pigment epithelial layer in the pathway of discrete ion migration. Insertion into or through the highly vascular choroid of the posterior pole, severe subchoroidal, intraretinal and or intraorbital hemorrhage would likely have resulted along with disruption of blood flow to the posterior pole.

A photovoltaic device artificial retina is also disclosed in U.S. Pat. No. 5,024,223. That device was inserted into the potential space within the retina itself. That space, called the subretinal space, is located between the outer and inner layers of the retina. The photovoltaic device was comprised of a plurality of microphotodiodes deposited on a single silicon crystal substrate. They transduced light into small electric currents that stimulated overlying and surrounding inner retinal cells. Due to the solid substrate nature of the microphotodiodes, blockage of nutrients from the choroid to the inner retina occurred. The presence of holes of various geometries was not helpful to permeation of oxygen and biological substances.

Another method for a photovoltaic artificial retina device is reported in U.S. Pat. No. 5,397,350. That device was comprised of a plurality of microphotodiodes, disposed within a liquid vehicle, for placement into the subretinal space of the eye. Because of the open spaces between adjacent microphotodiodes, nutrients and oxygen flowed from the outer retina into the inner retinal layers nourishing those layers. In another embodiment, each microphotodiodes included an electrical capacitor layer.

U.S. Pat. No. 5,935,155, issued to Humayun, et al., describes a visual prosthesis and method of use. The '155 patent includes a camera, signal processing electronics, and an epiretinal mounted retinal electrode array. The retinal array is mounted inside the eye to the retina using tacks, magnets, or adhesives. A small ribbon cable coupling the circuitry to the electrode array pierces the sclera. A portion of the device is attached to the outside of the sclera. U.S. Pat. No. 5,935,155 is incorporated herein by reference in its entirety.

Chow, et al., in U.S. Pat. No. 6,427,087 discloses a transretinal approach to artificial retinal stimulation. An artificial retinal device comprised of photodiodes, implanted in the subretinal space of the eye in persons with certain types of retinal blindness, induced artificial vision by electrical stimulation of the remaining viable cells of the retina. The artificial retina includes a stimulating electrode unit and an extension that houses an electrical return ground electrode unit that may be placed in the vitreous cavity.

Nisch, et al., in U.S. Patent Pub. No. US2002/0198573, describes a subretinal implant with a receiver coil positioned on the eye ball outside the sclera. The sclera incision is made somewhat below the lateral eye muscle.

A technique is needed that does not cut through the choroid and that minimizes damage to the retina during surgical implantation of subretinal implants.

Drug Delivery to the Eye

Treatment of the eye by direct or local release of the drug into the inside of the eye offers advantages for treatment of certain diseases of the eye. One advantage is that dosages may be lower that treatment of an eye disease by another method. Additionally it offers advantages of direct application of the drug to tissue requiring chronic treatment.

Various drugs have been developed to assist in the treatment of a wide variety of ailments and diseases. However, in many instances such drugs are not capable of being administered either orally or intravenously without the risk of various detrimental side effects. Systems for administering such drugs have been developed, many of which provide a release rate that reduces the occurrence of detrimental side effects. For example, intravenous ganciclovir (GCV) is effective in the treatment of CMV retinitis in AIDS patients, but bone marrow toxicity limits its usefulness. It is further limited by the risk of sepsis related to permanent indwelling catheters and the inability to receive concurrent therapy with zidovudine (AZT).

One approach utilizes implantable microfluidic delivery systems, as the microchip drug delivery devices of Santini, et al. (U.S. Pat. No. 6,123,861) and Santini, et al. (U.S. Pat. No. 5,797,898) or fluid sampling devices, must be impermeable and they must be biocompatible. Greenberg, et al. in U.S. patent application Ser. No. 10/046458 and Greenberg, et al. in U.S. patent application Ser. No. 10/096,183 present novel implantable microfluidic delivery systems for drugs and other materials, both of which are incorporated herein by reference in their entirety. The devices must not only exhibit the ability to resist the aggressive environment present in the body, but must also be compatible with both the living tissue and with the other materials of construction for the device itself. The materials are selected to avoid both galvanic and electrolytic corrosion.

In microchip drug delivery devices, the microchips control both the rate and time of release of multiple chemical substances and they control the release of a wide variety of molecules in either a continuous or a pulsed manner. A material that is impermeable to the drugs or other molecules to be delivered and that is impermeable to the surrounding fluids is used as the substrate. Reservoirs are etched into the substrate using either chemical etching or ion beam etching techniques that are well known in the field of microfabrication. Hundreds to thousands of reservoirs can be fabricated on a single microchip using these techniques.

The physical properties of the release system control the rate of release of the molecules, e.g., whether the drug is in a gel or a polymer form. The reservoirs may contain multiple drugs or other molecules in variable dosages. The filled reservoirs can be capped with materials either that degrade or that allow the molecules to diffuse passively out of the reservoir over time. They may be capped with materials that disintegrate upon application of an electric potential. Release from an active device can be controlled by a preprogrammed microprocessor, remote control, or by biosensor. Valves and pumps may also be used to control the release of the molecules.

A reservoir cap can enable passive timed release of molecules without requiring a power source, if the reservoir cap is made of materials that degrade or dissolve at a known rate or have a known permeability. The degradation, dissolution or diffusion characteristics of the cap material determine the time when release begins and perhaps the release rate.

Alternatively, the reservoir cap may enable active timed release of molecules, requiring a power source. In this case, the reservoir cap consists of a thin film of conductive material that is deposited over the reservoir, patterned to a desired geometry, and serves as an anode. Cathodes are also fabricated on the device with their size and placement determined by the device's application and method of electrical potential control. Known conductive materials that are capable of use in active timed-release devices that dissolve into solution or form soluble compounds or ions upon the application of an electric potential, including metals, such as copper, gold, silver, and zinc and some polymers.

When an electric potential is applied between an anode and cathode, the conductive material of the anode covering the reservoir oxidizes to form soluble compounds or ions that dissolve into solution, exposing the molecules to be delivered to the surrounding fluids. Alternatively, the application of an electric potential can be used to create changes in local pH near the anode reservoir cap to allow normally insoluble ions or oxidation products to become soluble. This allows the reservoir cap to dissolve and to expose the molecules to be released to the surrounding fluids. In either case, the molecules to be delivered are released into the surrounding fluids by diffusion out of or by degradation or dissolution of the release system. The frequency of release is controlled by incorporation of a miniaturized power source and microprocessor onto the microchip.

One solution to achieving biocompatibility, impermeability, and galvanic and electrolytic compatibility for an implanted device is to encase the device in a protective environment. It is well known to encase implantable devices with glass or with a case of ceramic or metal. Schulman, et al. (U.S. Pat. No. 5,750,926) is one example of this technique. It is also known to use alumina as a case material for an implanted device as disclosed in U.S. Pat. No. 4,991,582. Santini, et al. (U.S. Pat. No. 6,123,861) discuss the technique of encapsulating a non-biocompatible material in a biocompatible material, such as poly(ethylene glycol) or polytetrafluoroethylene-like materials. They also disclose the use of silicon as a strong, non-degradable, easily etched substrate that is impermeable to the molecules to be delivered and to the surrounding living tissue. The use of silicon allows the well-developed fabrication techniques from the electronic microcircuit industry to be applied to these substrates. It is well known, however, that silicon is dissolved when implanted in living tissue or in saline solution.

An alternative approach to microfluidic devices is, for example, is an orally administered pill or capsule that contains a drug encapsulated within various layers of a composition that dissolves over a period of time in the digestive tract, thereby allowing a gradual or slow release of the drug into the system.

Another type of device for controlling the administration of such drugs is produced by coating a drug with a polymeric material permeable to the passage of the drug to obtain the desired effect. Such devices are particularly suitable for treating a patient at a specific local area without having to expose the patient's entire body to the drug. This is advantageous because any possible side effects of the drug could be minimized.

Such systems are particularly suitable for treating ailments affecting the eye. Advances for administering a drug to the external surface of the eye are disclosed in U.S. Pat. No.

4,014,335 to Arnold. Arnold describes various ocular inserts that act as a deposit or drug reservoir for slowly releasing a drug into the tear film for prolonged periods. These inserts are fabricated of a flexible polymeric material that is biologically inert, non-allergenic, and insoluble in tear fluid. To initiate the therapeutic programs of these devices, the ocular inserts are placed in the cul-de-sac between the sclera of the eyeball and the eyelid for administering the drug to the eye.

Devices formed of polymeric materials that are insoluble in tear fluid retain their shape and integrity during the course of the needed therapy to serve as a drug reservoir for continuously administering a drug to the eye and the surrounding tissues at a rate that is not effected by dissolution or erosion of the polymeric material. Upon termination of the desired therapeutic program, the device is removed from the cul-de-sac.

Another type of device used for sustained release of a drug to the external surface of the eye, described in U.S. Pat. No. 3,416,530, is manufactured with a plurality of capillary openings that communicate between the exterior of the device and the interior chamber generally defined from a polymeric membrane. While these capillary openings in this construction are effective for releasing certain drugs to the eye, they add considerable complexity to the manufacture of the device because it is difficult to control the size of these openings in large-scale manufacturing using various polymers.

Another device, described in U.S. Pat. No. 3,618,604, does not involve such capillary openings, but instead provides for the release of the drug by diffusion through a polymeric membrane. The device, in a preferred embodiment, as disclosed in that patent, comprises a sealed container having the drug in an interior chamber. Nonetheless, as described in U.S. Pat. No. 4,014,335, certain problems have been identified with such devices such as the difficult task of sealing the margins of the membrane to form the container. In addition, stresses and strains introduced into the membrane walls from deformation during manufacturing of those devices may cause the reservoir to rupture and leak.

Another such device, described in U.S. Pat. No. 4,014,335, comprises a three-layered laminant having a pair of separate and discrete first and third walls formed of a material insoluble in tear fluid with one of the walls formed of a drug release material permeable to the passage of drug and the other wall formed of a material impermeable to the passage of the drug.

Smith, U.S. Pat. No. 5,378,475, discusses sustained release drug delivery devices for selected areas wherein release of the drug is allowed to pass through the device in a controlled manner by using permeable coatings. Parel, U.S. Pat. No. 5,098,443, describes methods of implanting intraocular and intraorbital devices for controlled release of drugs as a polymer biodegrades or as the implant releases the drug by osmosis.

The above described systems and devices are intended to provide sustained release of drugs effective in treating patients at a desired local or systemic level for obtaining certain physiological or pharmacological effects. However, there are many disadvantages associated with their use including the fact that it is often difficult to obtain the desired release rate of the drug. The need for a better release system is especially significant in the treatment of CMV retinitus.

Further situations that would benefit from an improved drug delivery device for the interior of an eye include neurotrophic factors, anti-inflammatory, anti-angiogenic (e.g., anti-vegf), anti-viral, anti-bacterial, and anti-neoplastic (i.e., anti cancer) drugs. These various treatments might benefit visual impairment, caused, for example, by outer retinal blindness, glaucoma, macular degeneration, diabetic retinopathy, reinitis, and uveitis, to name a few. Thus, there remains a long-felt need in the art for an improved system for providing sustained release of a drug to a patient in order to obtain a desired local or systemic physiological or pharmacological effect. In addition, all of these devices release their drug into the tear film. If relatively high levels are required inside the eye, such devices are ineffective.

Obviously, many modifications and variations of the present invention are possible in light of the above teachings. It is therefore to be understood that, within the scope of the appended claims, the invention may be practiced otherwise than as specifically described.

SUMMARY OF THE INVENTION

The present invention is directed to an implantable device and method of manufacture of the implantable device to affect an eye, the eye having a retina, a sclera, a vitreous cavity, and a choroid. In one preferred embodiment the retinal implant is positioned subretinally; the retinal implant made up of at least one electrode connected with a stimulating source; at least one connection with the stimulating source and the at least one electrode, where the connection passes transretinally into the vitreous cavity of the eye; the connection having been designed to pass through the sclera at a point where there is no retina; and the stimulating source located outside the eye.

The novel features of the invention are set forth with particularity in the appended claims. The invention will be best understood from the following description when read in conjunction with the accompanying drawings.

OBJECTS OF THE INVENTION

It is an object of the invention to provide a subretinal implant, suitable to enable vision, with a transretinal electrical lead that passes through the sclera where there is no retina.

It is an object of the invention to manufacture an implant with a transretinal electrical lead suitable for subretinal placement in a living eye and that passes through the sclera at a point where there is no retina.

It is an object of the invention to provide a drug treatment device that is suitable for placement subretinally with a drug source that is located outside the eye and with a delivery tube that passes through the sclera at a point where there is no retina.

Other objects, advantages and novel features of the present invention will become apparent from the following detailed description of the invention when considered in conjunction with the accompanying drawing.

DETAILED DESCRIPTION OF THE PREFERRED EMBODIMENT

Figure 1:
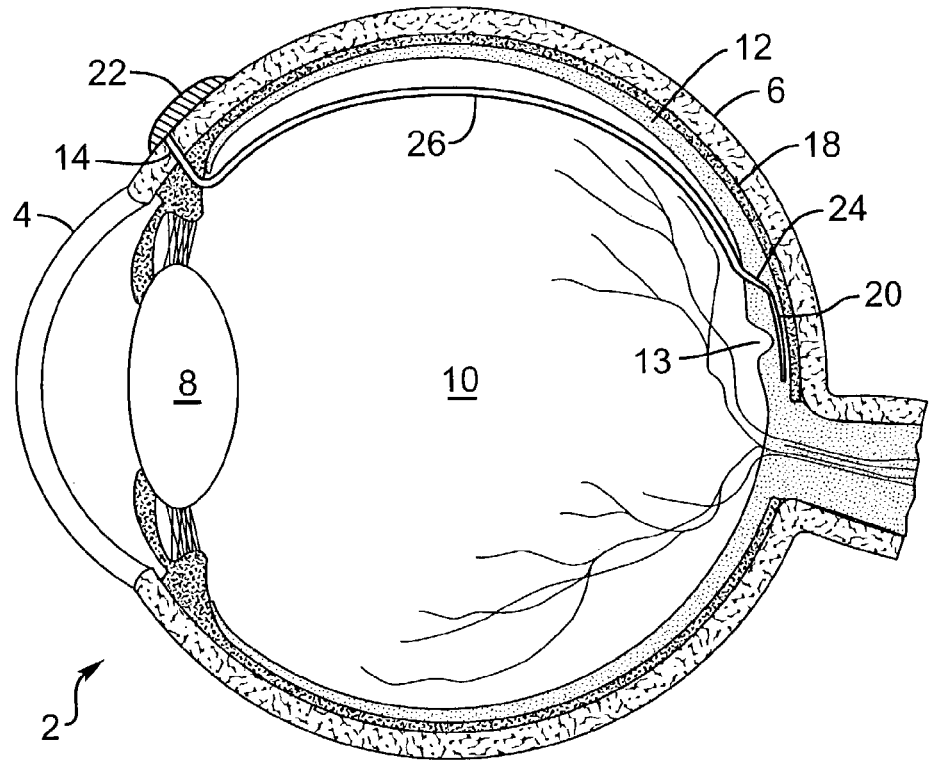
FIG. 1 illustrates a cross-sectional view of an eye showing the placement of the retinal implant and associated electronics.

FIG. 1 provides a cross-sectional view of a preferred embodiment of the eye 2 with a retinal implant 20 placed subretinally. The current invention involves the use of an electronic device, a retinal implant 20 that is capable of mimicking the signals that would be produced by a normal inner retinal photoreceptor layer. When the device is implanted subretinally between the inner and outer retinal layers, it will stimulate the inner layer to provide significantly useful formed vision to a patient whose eye no longer reacts to normal incident light on the retina 12. Patient's having a variety of retinal diseases that cause vision loss or blindness by destruction of the vascular layers of the eye, including the choroid, choriocapillaris, and the outer retinal layers, including Bruch's membrane and retinal pigment epithelium. Loss of these layers is followed by degeneration of the outer portion of the inner retina, beginning with the photoreceptor layer. The inner retina, composed of the outer nuclear, outer plexiform, inner nuclear, inner plexiform, ganglion cell and nerve fiber layers, may remain functional. Functioning of the inner retina allows electrical stimulation of this structure to produce sensations of light or even vision.

The biocompatible retinal implant 20 is attached by an electrically conductive cable or lead wire 26 that is also biocompatible, to a control electronics 22 package that contains suitable electronics to generate an electrical signal that is transmitted along a lead wire 26 to the retinal implant, which stimulates the retina 12.

The eye 2 has a cornea 4, lens 8, and vitreous cavity 10 through which light normally passes, prior to striking the retina 12 and causing vision. The eye 2 has an outer layer, called the sclera 6, and a nutrient rich layer, called the choroid 18, that is located between the retina 12 and the sclera 6.

In a preferred embodiment, the retinal implant 20 is located subretinally near the fovea 13 to provide good electrical contact between the retinal implant and the retina 12. The lead wire 26, which is attached to the retinal implant 20, proceeds transretinally through retina 12 via retinal incision 24. Passing the lead wire into the vitreous cavity 10 via the retinal incision 24 avoids disrupting the delicate choroid 18, and thereby avoids interfering with the supply of nutrients to the retina 12. The lead wire 26 passes through the vitreous cavity to a point near the front of the eye 2 where it traverses transsclera via an incision 14 through the sclera 6 at a point where the retina 12 and choroid 18 are not present, thereby further avoiding disruption to the blood supply, oxygen, and nutrients that are needed to sustain the retina 12. While the choroid 18 does extend to this region of the eye near the lens 8, called the pars plana, choroid 18 bleeding will not damage the retina 12, and is far less likely to spread to the central retina 12, called the macula, which is the area of most sensitive vision, while choroid 18 bleeding under the retina 12 can track along the retina 12 and end up damaging the macular region near the forvea 13 of the retina 12.

The control electronics 22 are located outside the eye 2 and are attached to lead wire 26. The control electronics 22 are preferably attached to the sclera 6 by sutures. In alternative embodiments, the control electronics 22 are located distant from the eye 2.

Figure 2:
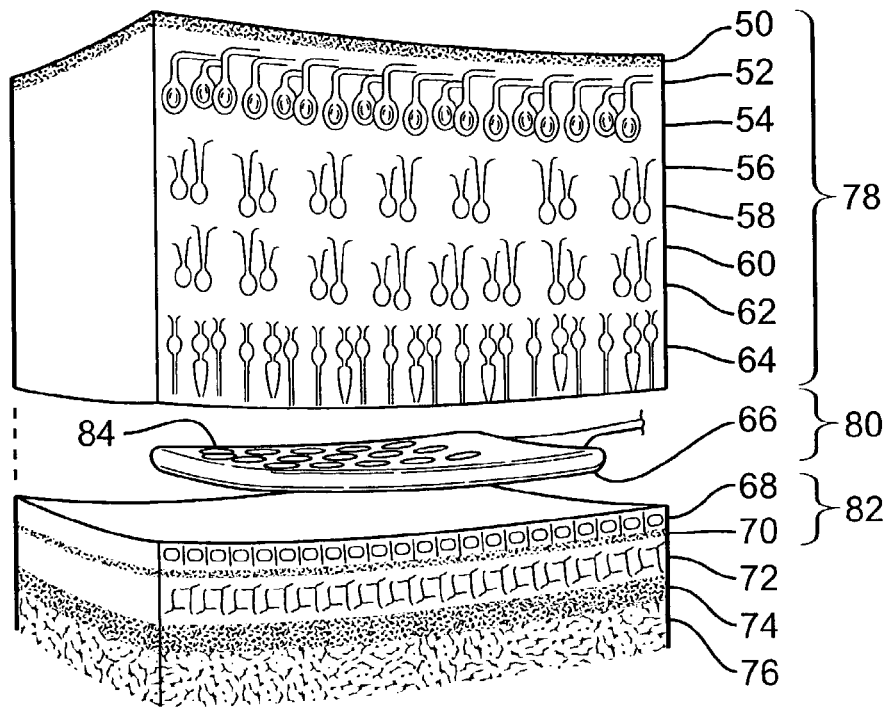
FIG. 2 illustrates a cross-sectional view of a retina showing the tissue layers and placement of the retinal implant in the retina for electrical stimulation of the retina.

A perspective cross-sectional view of the retina and outer wall of the eye is presented in FIG. 2. Moving from the inside of the eye outward, the structure of the eye is encountered as follows: internal limiting membrane 50, axons 52, ganglion and amacrine cell layer 54, inner plexiform 56, inner nuclear layer 58, outer plexiform layer 60, bipolar cell layer 62, photoreceptor cell layer 64, retinal pigment epithelium 68, Bruck's membrane 70, choriocapillaris 72, choroid 74, and the outer coat or sclera 76.

The inner retina 78 is generally the structures from the internal limiting membrane 50 to the photoreceptor cell layer 64. The outer retinal layer 82 consists of the retinal pigment epithelium 68 and Bruck's membrane 70.

A subretinal implant position 80 is located between the photoreceptor cell layer 64 and the retinal pigment epithelium 68. In a preferred embodiment, the retinal implant 66 is surgically implanted in the subretinal implant position 80.

In a preferred embodiment, the retinal implant 66 is biocompatible and contains a number of arrayed electrodes 84, which are electrically stimulated by an outside source to stimulate the inner retinal layer 78, thereby to provide significantly useful formed vision. It is preferred that the electrodes 84 are located on the surface of the retinal implant 66 that faces the front of the eye, to stimulate the inner retinal layer 78.

Figure 3:
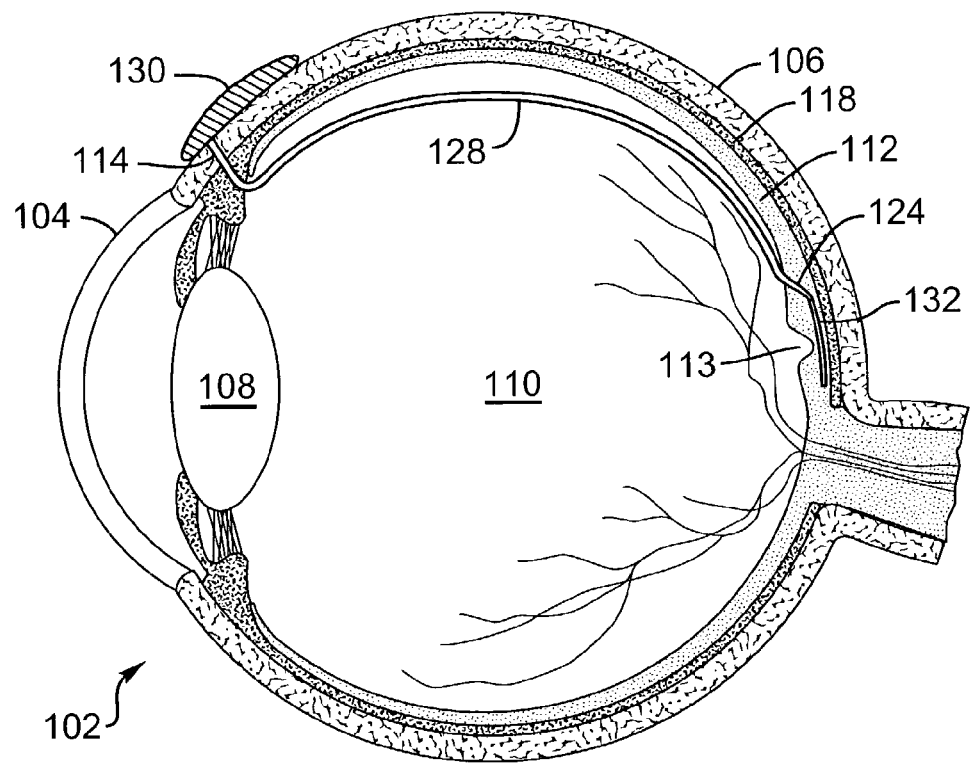
FIG. 3 illustrates a cross-sectional view of an eye showing placement of the retinal implant for drug delivery.

A cross-sectional view of the eye 102 and retinal implant 132 is presented in FIG. 3. In this embodiment of the invention, drugs are delivered by transfer from drug reservoir 130 to retinal implant 132, where the drugs are released subretinally for treatment of the tissue of the eye 102 and especially the retinal tissue. This device is particularly advantageous for treatment of chronic issues. A further advantage is that the quantity of drugs required and released to the eye is minimized by releasing the drugs in near proximity to the area of the eye 102 that requires treatment.

In a preferred embodiment, the drugs are transferred from drug reservoir 130 via delivery conduit 128, which is preferably a tube, to retinal implant 132. While the drugs may be pumped or delivered by other known means, it is preferable that they be delivered electrophoretically.

The structure of the eye 102, as shown in FIG. 3, presents a cornea 104 at the front of the eye with a lens 108 behind. The sclera 106 is on the outside of the eye and the choroids 118 is inside the eye 102 between the retina 112 and sclera 106.

The retinal implant 132 is implanted subretinally, preferably near the back of the eye. It is shown near the fovea 113, in FIG. 3, but may be located at other subretinal locations, as desired. The drug delivery conduit 128 connects the retinal implant 132 with the drug reservoir 130. The conduit 128 passes transretinally through retinal incision 124 and enters the vitreous cavity 110. The conduit 128 then passes transsclera at sclera incision 114, that passes through the sclera at a location near the front of the eye where there is no retina 112, thereby avoiding damage to the nutrient rich choroid 118 and avoiding disruption of the blood supply to the retina 112.

Figure 4:
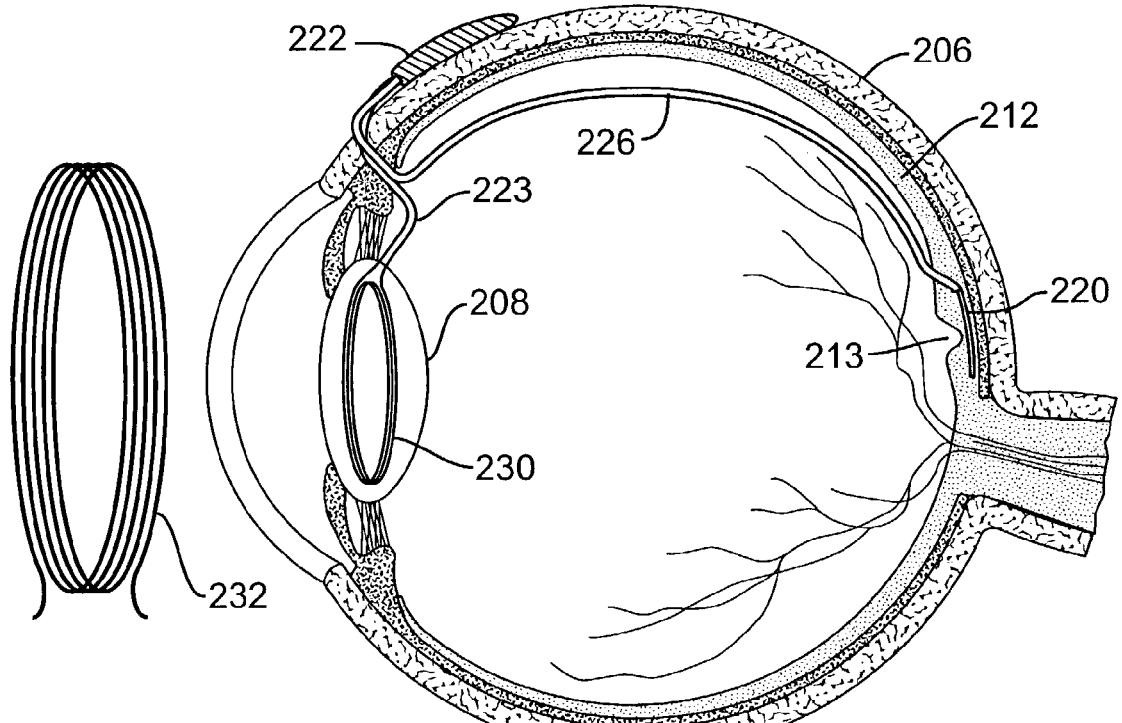
FIG. 4 illustrates a cross-sectional view of an eye showing the placement of the subretinal implant.

An alternative embodiment of a retinal implant to enable vision restoration is presented in FIG. 4, wherein a cross-section of the eye is presented showing the lens 208, retina 212, sclera 206, and fovea 213. U.S. Pat. No. 5,935,155, issued to Humayun, et al., the '155 patent, describes a similar visual prosthesis and method of use. In this embodiment, the retinal implant 220 is implanted subretinally. A primary coil 232 is located preferably either in an eyeglass lens frame or in a soft contact lens. This coil 232 is used to inductively couple the radio frequency encoded image signal to the secondary coil 230 that, in this embodiment, is implanted behind the iris of the eye. The control electronics 222 is placed in a hermetically sealed package and is coupled to a secondary coil 230 by a coil lead 223 that pierces the sclera 206 at a point near the lens 208 where there is no retina 212. The control electronics 222 is attached to the outside of the sclera 206. A lead wire 226 coupling the control electronics 222 to the retinal implant 220 passes transsclera at a point where there is no retina, preferably near the lens 208. The lead wire 226 passes inside the eye, preferably along the interior wall of the eye, and pierces the retina to pass transretinal to couple the control electronics 222 to the retinal implant 220. This invention is an improvement over that disclosed by the '155 patent because the retinal implant is subretinal rather than epiretinal, thereby facilitating stimulation of the retinal tissue.

Figure 5:
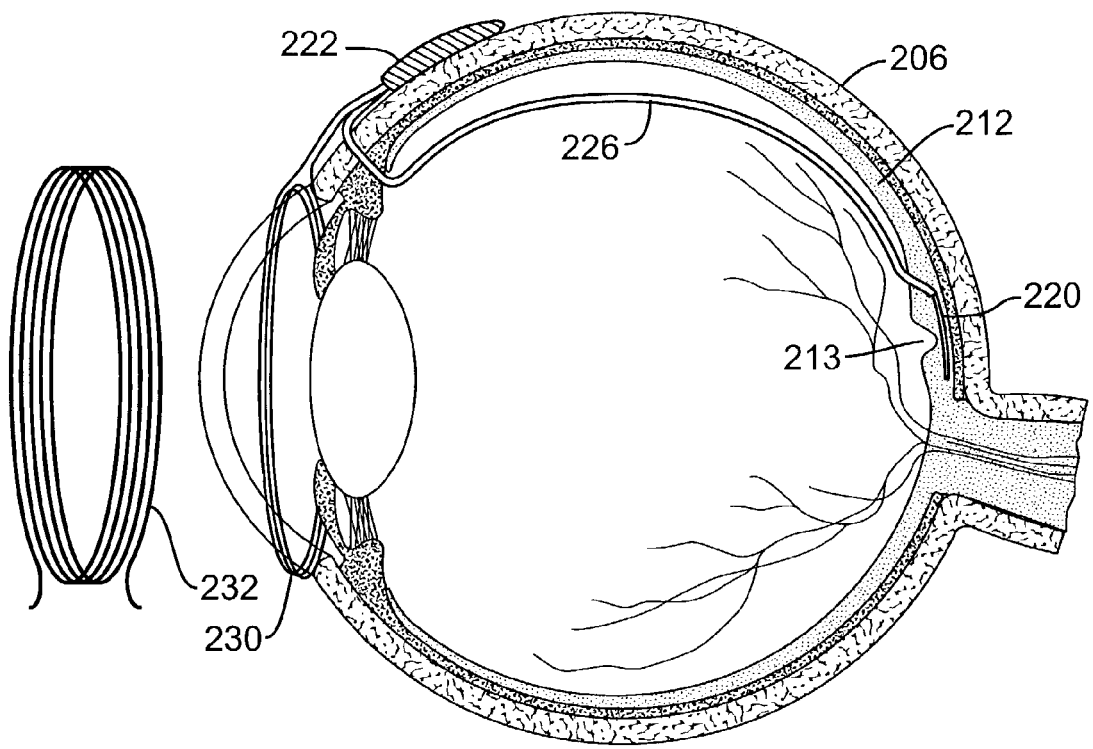
FIG. 5 illustrates a cross-sectional view of an eye showing the placement of the subretinal implant.

A further alternative embodiment of a retinal implant to enable vision restoration is presented in FIG. 5. The '155 patent discloses a similar invention, wherein the retinal implant 220 is placed subretinally. In this embodiment, the secondary 230 is attached to the sclera 206 instead of being implanted within the eye. As with the control electronics 222, the attachment of the secondary coil 230 to the sclera 206 may be by suturing or other appropriate means, as discussed in the '155 patent. In this way, only the lead wire 226 which attaches the control electronics 222 to the retinal implant 220 mounted subretinally below retina 212 is required to pierce the sclera 206. The extra-ocular attachment of the control electronics 222 allows increased access to this circuitry that eases the replacement or updating of these components.

Figure 6:
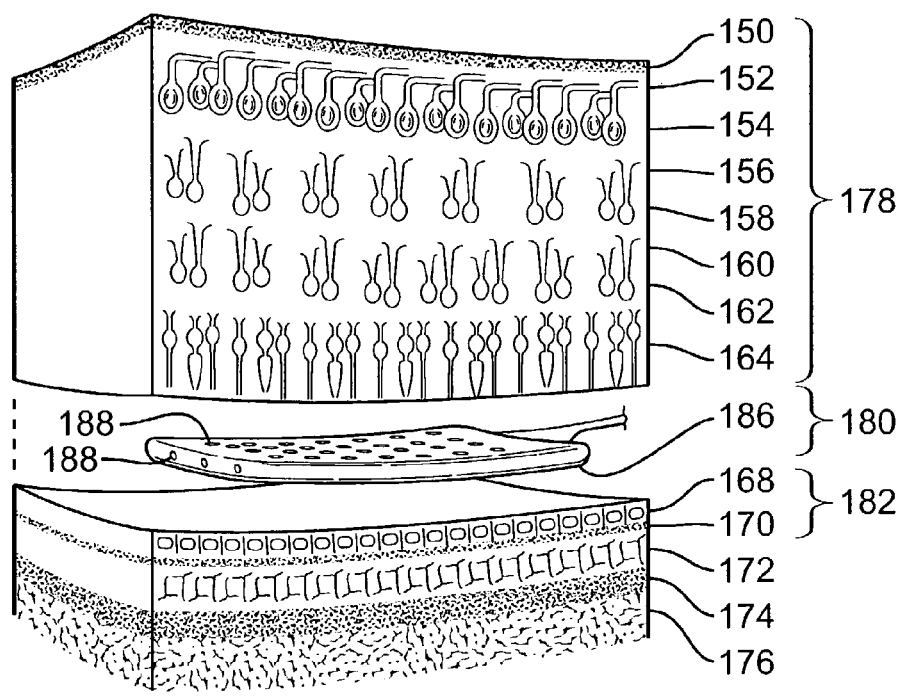
FIG. 6 illustrates a cross-sectional view of a retina showing the tissue layers and placement of the retinal implant in the retina for drug delivery.

FIG. 6 presents a perspective cross-sectional view of the retina and outer wall of the eye. The tissue layers from the inside of the eye outward are the internal limiting membrane 150, axons 152, ganglion and amacrine cell layer 154, inner plexiform 156, inner nuclear layer 158, outer plexiform layer 160, bipolar cell layer 162, photoreceptor cell layer 164, retinal pigment epithelium 168, Bruck's membrane 170, choriocapillaris 172, choroid 174, and sclera 176.

The inner retinal layer 178 is comprised of tissue from the internal limiting membrane 150 to the photoreceptor cell layer 164. The outer retinal layer 182 consists of the retinal pigment epithelium 168 and Bruck's membrane 170.

Between the inner retinal layer 178 and outer retinal layer 182, is the subretinal implant position 180 in which retinal implant 186 is surgically located.

The retinal implant contains a number of orifices 188 through with the drug is released into the surrounding retinal tissue. The orifices 188 are preferably uniformly presented on both the inner and outer surfaces as well as on the edges of the retinal implant 186. However, the orifices 188 may be preferentially oriented in the retinal implant 186 to selectively release the drug on or near a desired tissue or location.

Obviously, many modifications and variations of the present invention are possible in light of the above teachings. It is therefore to be understood that, within the scope of the appended claims, the invention may be practiced otherwise than as specifically described.

What is claimed is:

1. A method for producing an artificial retinal device suitable to electrically stimulate a retina of an eye to produce artificial vision, the eye having a sclera, a macula including a fovea and a vitreous cavity, said method comprising the steps of:

selecting a biocompatible retinal implant;

placing at least one stimulating electrode in said retinal implant that is suitable for electrically stimulating the retina;

positioning the retinal implant in a subretinal position within the macula near the fovea in the eye;

connecting an electrical lead to said stimulating electrode;

passing said electrical lead transretinally into the vitreous cavity of the eye;

attaching said electrical lead to an electrical source that is located outside the eye; and passing said electrical lead through the sclera at a point where there is no retina.

2. The method according to claim 1, wherein the retinal implant is disposed between the fovea and a choroid.

3. The method according to claim 1, wherein the fovea is disposed substantially between the retinal implant and a cornea.

4. A method for producing artificial vision in an eye using an artificial retinal device, the eye having a sclera, a retina, a fovea in a macula and a vitreous cavity, wherein said artificial retinal device comprises a retinal implant further comprising at least one stimulating electrode in said retinal implant, said stimulating electrode connected with an electrical source, at least one electrical lead connected with said electrical source and said electrode, the method comprising the steps of:

positioning the retinal implant inside the macula in a subretinal position near the fovea in the eye;

passing said electrical lead transretinally through the retina of the eye into the vitreous cavity; and passing said electrical lead through the sclera at a point where there is no retina.

5. The method according to claim 4 further comprising the step of attaching said electrical source to the sclera by sutures.

6. The method according to claim 4 further comprising the step of positioning said electrodes to face the retina.

7. The method according to claim 4, wherein the retinal implant is disposed between the fovea and a choroid.

8. The method according to claim 4, wherein the fovea is disposed substantially between the retinal implant and a cornea.

9. A method for producing artificial vision in an eye using an artificial retinal device, the eye comprising a sclera, a choroid, and a retina, the eye further comprising a vitreous cavity and a macula, the artificial retinal device comprising a retinal implant, an electrical source, and an electrical lead connecting said retinal implant and said electrical source, wherein the retinal implant comprises at least one stimulating electrode, the at least one stimulating electrode connected to the electrical source through the electrical lead, the method comprising:

positioning the retinal implant in the eye subretinally within the macula;

passing a first end of the electrical lead through the retina, the first end of the electrical lead connected to the stimulating electrode;

passing a second end of the electrical lead through the sclera at a point where there is no retina, the second end of the electrical lead connected to the electrical source; and positioning the electrical source outside the eye.

10. The method of claim 9, wherein the retinal implant comprises a number of arrayed electrodes electrically stimulated by the electrical source to stimulate the retina.

11. The method of claim 9, wherein the number of arrayed electrodes are located on the surface of the retinal implant that faces the retina.

12. The method of claim 9, wherein passing the second end of the electrical lead through the sclera at a point where there is no retina, is performed at a point where there is no choroid.

13. The method of claim 9, wherein positioning the electrical source outside the eye is performed by attaching the electrical source to the sclera outside the eye.

14. A method for producing artificial vision in an eye using an artificial retinal device, the eye comprising a retina substantially consisting of an inner retina and an outer retina, the eye further comprising a pars plana, a vitreous cavity, a macula and a fovea, the fovea located inside the macula, the artificial retinal device comprising a retinal implant, an electrical source, and an electrical lead connecting said retinal implant and said electrical source, wherein the retinal implant comprises at least one stimulating electrode, and the electrical lead has a first end connected to said at least one stimulating electrode and a second end connected to said electrical source, the method comprising:

positioning the retinal implant in the macula near the fovea between the inner retina and the outer retina;

positioning the electrical lead into the vitreous cavity, with the first end passing through the inner retina and the second end passing through the pars plana; and positioning the electrical source outside the eye.

15. A method for enabling vision restoration in an eye using an artificial device, the eye comprising a sclera, a choroid, and a retina, the eye further comprising an iris, a lens, a vitreous cavity, a macula and a fovea, the fovea located inside the macula, the artificial device comprising a retinal implant, an electrical source, means for transmitting an encoded image signal, means for decoding the encoded image signal, the means for decoding the encoded image signal connected to the electrical source, and a first electrical lead connecting the retinal implant and the electrical source, the method comprising:

positioning the retinal implant in the eye subretinally within the macula near the fovea;

positioning the first electrical lead into the vitreous cavity, a first end of the first electrical lead connected to the retinal implant passing through the retina and a second end of the electrical lead connected to the electrical source passing through the sclera at a point of the eye where there is no retina;

positioning the means for decoding the encoded image signal in a suitable position inside or outside the eye;

positioning the means for transmitting the encoded image signal outside the eye; and positioning the electrical source outside the eye.

16. The method of claim 15, wherein, the means for transmitting the encoded image signal is a primary coil and the means for decoding the encoded image signal is a secondary coil.

17. The method of claim 16, wherein the means for decoding the encoded image signal is located in the lens and the first end of the second electrical lead is connected to the means for decoding the encoded image signal through the lens.

18. The method of claim 16, wherein the second end of the second electrical lead is connected to the electrical source through the sclera at a point of the eye where there is no choroid.

19. The method of claim 15, wherein the means for decoding the encoded image signal is located inside the eye behind the iris, the artificial device further comprising a second electrical lead connecting the means for decoding the encoded image signal to the electrical source, the method further comprising:

positioning the second electrical lead in the vitreous cavity, a first end of the second electrical lead connected to the means for decoding the transmitted visual signal output, a second end of the second electrical lead connected to the electrical source through the sclera at a point of the eye where there is no retina.

20. The method of claim 15, wherein the second end of the first electrical lead is connected to the electrical source through the sclera at a point of the eye where there is no choroid.

21. A method for enabling vision restoration in an eye using an artificial device, the eye comprising a sclera, and a retina, the retina substantially consisting of an inner retina and an outer retina, the eye further comprising a cornea, an iris, a vitreous cavity, a macula and a fovea, the fovea located inside the macula, the artificial device comprising a retinal implant, an electrical source, a primary coil, a secondary coil, and a first electrical lead connecting the retinal implant and the electrical source, the primary coil suitable to inductively couple an encoded image signal to the secondary coil, the secondary coil connected to the electrical source, the method comprising:

positioning the retinal implant in the eye within the macula near the fovea between the inner retina and the outer retina;

positioning the first electrical lead into the vitreous cavity, a first end of the first electrical lead connected to the retinal implant passing through the retina and a second end of the electrical lead connected to the electrical source passing through the sclera at a point of the eye where there is no retina;

positioning the secondary coil in a suitable position inside or outside the eye;

positioning the primary coil outside the eye;

positioning the electrical source outside the eye; and providing an encoded image signal to the primary coil.

22. The method of claim 21, wherein the secondary coil is located outside the eye on the cornea.

23. The method of claim 21, wherein the secondary coil is located inside the eye behind the iris.

24. The method of claim 23, wherein the artificial device further comprises a second electrical lead connecting the secondary coil to the electrical source, the method further comprising:

positioning the second electrical lead in the vitreous cavity, a first end of the second electrical lead connected to secondary coil, a second end of the second electrical lead connected to the electrical source through the sclera at a point of the eye where there is no retina.

25. The method of claim 24, wherein the second end of the second electrical lead is connected to the electrical source through the sclera at a point of the eye where there is no choroid.

26. The method of claim 21, wherein the second end of the first electrical lead is connected to the electrical source through the sclera at a point of the eye where there is no choroid.

27. A method for producing an artificial retinal device suitable to electrically stimulate a retina of an eye to produce artificial vision, the eye having a sclera, a macula and a vitreous cavity, said method comprising the steps of:
  selecting a biocompatible retinal implant;
  placing at least one stimulating electrode in said retinal implant that is suitable for electrically stimulating the retina;
  positioning the retinal implant in a subretinal position within the macula in the eye;
  connecting an electrical lead to said stimulating electrode;
  passing said electrical lead transretinally into the vitreous cavity of the eye;
  attaching said electrical lead to an electrical source that is located outside the eye; and
  passing said electrical lead through the sclera at a point where there is no retina.

28. the method of claim 27, wherein positioning the retinal implant in a subretinal position is performed by positioning said retinal implant between the inner retina and the outer retina.

* * * * *